US008900611B2

(12) United States Patent
Hojo et al.

(10) Patent No.: US 8,900,611 B2
(45) Date of Patent: *Dec. 2, 2014

(54) SUSTAINED RELEASER COMPRISING SEX PHEROMONE SUBSTANCES

(75) Inventors: Tatsuya Hojo, Joetsu (JP); Kinya Ogawa, Tokyo (JP); Noboru Aiba, Joetsu (JP); Takehiko Fukumoto, Joetsu (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 239 days.

This patent is subject to a terminal disclaimer.

(21) Appl. No.: 11/226,588

(22) Filed: Sep. 14, 2005

(65) Prior Publication Data

US 2006/0057177 A1 Mar. 16, 2006

(30) Foreign Application Priority Data

Sep. 15, 2004 (JP) .................................. 2004-268628

(51) Int. Cl.
| A01N 25/00 | (2006.01) |
| A01N 37/02 | (2006.01) |
| A01N 35/00 | (2006.01) |
| A01N 35/02 | (2006.01) |
| A01N 25/18 | (2006.01) |
| A01N 31/02 | (2006.01) |

(52) U.S. Cl.
CPC ................ *A01N 25/18* (2013.01); *A01N 37/02* (2013.01)
USPC ............. 424/405; 514/546; 514/693; 424/84

(58) Field of Classification Search
USPC .............................. 424/405, 84; 514/546, 693
See application file for complete search history.

(56) References Cited

U.S. PATENT DOCUMENTS

| 4,017,030 | A | | 4/1977 | Coplan et al. | |
| 4,575,458 | A | * | 3/1986 | Steck et al. ...................... | 424/84 |
| 4,600,146 | A | | 7/1986 | Ohno | |
| 4,734,281 | A | * | 3/1988 | Yamamoto et al. ........... | 424/408 |
| 4,923,119 | A | * | 5/1990 | Yamamoto et al. ............. | 239/55 |
| 5,278,141 | A | * | 1/1994 | Berliner ............................ | 512/3 |
| 5,316,148 | A | * | 5/1994 | Neumann et al. .......... | 206/484.1 |
| 5,501,033 | A | * | 3/1996 | Wefler ............................. | 43/131 |
| 5,759,561 | A | * | 6/1998 | Angst et al. .................... | 424/407 |
| 5,925,367 | A | * | 7/1999 | Angst et al. .................... | 424/405 |
| 6,216,960 | B1 | * | 4/2001 | Aiba et al. ....................... | 239/34 |
| 6,355,236 | B2 | * | 3/2002 | Ishino et al. ..................... | 424/84 |
| 6,419,943 | B1 | * | 7/2002 | Sakurada et al. .............. | 424/411 |
| 6,562,331 | B1 | * | 5/2003 | Ito et al. .......................... | 424/84 |
| 6,618,983 | B1 | * | 9/2003 | Spragins ........................ | 43/107 |
| 2005/0235400 | A1 | * | 10/2005 | Campbell et al. ................ | 2/406 |

FOREIGN PATENT DOCUMENTS

| DE | 2641630 A1 | | 8/1977 |
| EP | 0273197 A1 | | 7/1988 |
| EP | 0342126 A2 | | 11/1989 |
| EP | 0540932 A1 | | 5/1993 |
| EP | 0913088 A1 | | 5/1999 |
| EP | 0938842 A1 | | 9/1999 |
| EP | 1459626 A1 | * | 9/2004 |
| JP | 63-145201 A | | 6/1988 |
| JP | 2-69902 U | | 5/1990 |
| JP | 04243802 A | * | 8/1992 |
| JP | 06040808 A | * | 2/1994 |
| JP | 06040809 A | * | 2/1994 |
| JP | 06056608 A | * | 3/1994 |
| JP | 11-279011 | | 10/1999 |

OTHER PUBLICATIONS

Beevor PS, Hall DR, Lester R, Poppi RG, Read JS, and Nesbitt BF, "Sex Pheromones of the Armyworm Moth, *Spodoptera exempta* Walker," Experientia, vol. 31, No. 1, pp. 22-23 (Jan. 15, 1975).*
Clark JD, and Haynes KF, "Sex Attractant for the Bluegrass Webworm (Lepidoptera: Pyralidae)," Journal of Economic Entomology, vol. 83, No. 3, pp. 856-859 (Jun. 1990).*
Cork A, Murlis J, and Megenasa T, "Identification and Field Testing of Additional Components of Female Sex Pheromone of African Armyworm, *Spodoptera exempta* (Lepidoptera: Noctuidae)," Journal of Chemical Ecology, vol. 15, No. 4, pp. 1349-1364 (1989).*
Alza Corp. v. Mylan Laboratories Inc., 80 USPQ2d 1001-1009, 1004 (Fed. Cir. 2006).*
In re Kahn, 78 USPQ2d 1329-1339, 1336 (Fed. Cir. 2006).*

(Continued)

*Primary Examiner* — John Pak
*Assistant Examiner* — Nathan W Schlientz
(74) *Attorney, Agent, or Firm* — Myers Bigel Sibley & Sajovec, P.A.

(57) ABSTRACT

Provided are a sustained releaser of sex pheromone substances and a method for controlling insect pest by using the releaser, each enabling to control the simultaneous release of a mixture of sex pheromone substances having different chemical structures of one insect pest or a mixture of sex pheromone substances of insect pests, and each enabling to release the sex pheromone substances at a fixed rate or greater during the infestation period or periods of the respective insect pest or pests. More specifically, provided is a sustained releaser of sex pheromone substances comprising one or more first sex pheromone substances selected from linear aliphatic aldehyde having 10 to 18 carbon atoms, one or more second sex pheromone substances selected from aldehyde-free aliphatic derivatives having 7 to 20 carbon atoms, and first and second chambers each made of polymer material, wherein all of the first sex pheromone substances or all of the first sex pheromone substances and some of the second sex pheromone substances are enclosed in the first chamber and the remainder of the sex pheromone substances is enclosed in the second chamber.

1 Claim, 1 Drawing Sheet

(56) References Cited

OTHER PUBLICATIONS

J.M. Vakenti, A.P. Gaunce, K.N. Slessor, G.G.S. King, S.A. Allan, H.F. Madsen and J.H. Borden; Journal of Chemical Ecology, 1988, 14(2), 605-621.*

Alan Cork, Pheromone Manual, Natural Resources Institute, Chatham Maritime ME4 4TB, UK, 2004, Chapter 4: Pheromone Stability, p. 13.*

V. Mahadevan, "Reactions of Fatty Aldehydes With Fatty Alcohols: Formation of Acetals, Hemiacetals and Alk-l-enyl Alkyl Ethers", LIPIDS, 1970, vol. 5, No. 6, 563-565.*

European Search Report, corresponding to European Application No. 04101052.1, mailed Jul. 28, 2004.

Japanese Official Action corresponding to application No. 2004-268628, dated Jan. 6, 2010.

* cited by examiner

FIG.1(a)
FIG.1(b)
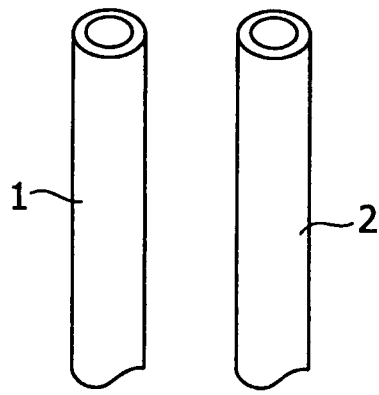
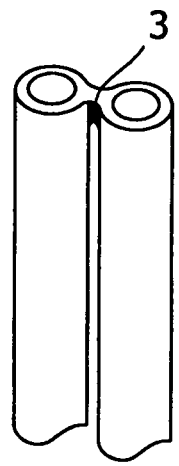
FIG.1(c)
FIG.1(d)
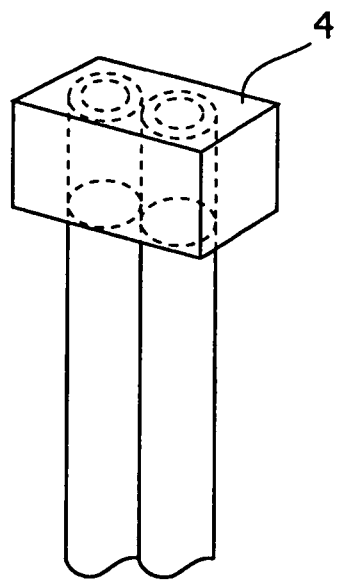
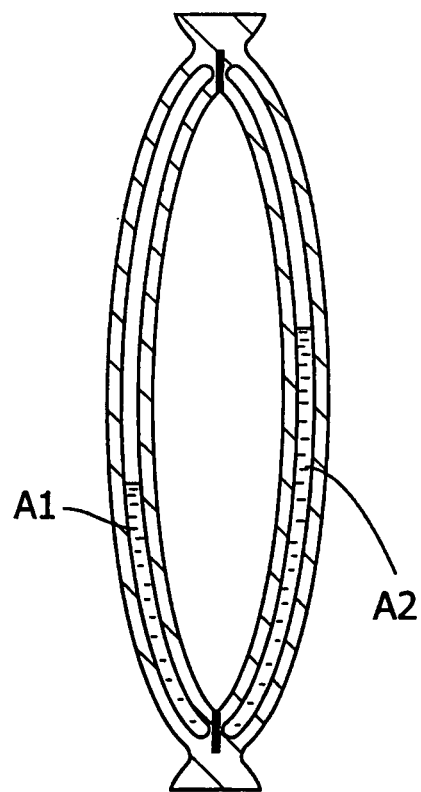

SUSTAINED RELEASER COMPRISING SEX PHEROMONE SUBSTANCES

RELATED APPLICATION

This application claims priority from Japanese Patent Application No. 2004-268628; filed Sep. 15, 2004, the disclosure of which is incorporated by reference herein in its entirety.

BACKGROUND OF THE INVENTION

1. Field of the Invention

The present invention relates to a sustained releaser and a pest control method each enabling simultaneous release of sex pheromone substances.

2. Description of the Related Art

Currently, as one of the most effective methods for utilizing a sex pheromone of an insect pest, the mating disruption method which confuses the mating behavior of the insect pest by retaining a chemically synthesized sex pheromone substance at a predetermined concentration or greater in a farm field has been developed to a practical stage. What is important in this method is development of a sustained release formulation releaser (dispenser) capable of releasing a synthesized sex pheromone substance for a long period of time at a fixed rate or greater and setting of a period required for mating disruption of an insect pest to be controlled.

In most cases, it may be relatively easy to control the release of a sex pheromone substance of a single insect pest at a fixed rate for a predetermined period, because it contains only one substance, or a plurality of substances which are similar in chemical structure. Some insect pests however have, as their sex pheromone substances, a plurality of compounds utterly different in chemical structure. It is difficult to enclose them in one releaser (dispenser) and control the release of them. In general, a certain crop rarely has a single insect pest fauna so that it is necessary in most cases to control a plurality of insect pests simultaneously, especially in an area having complex insect pest faunas such as Japan.

Difficulties in designing of a sustained releaser capable of simultaneously -releasing compounds different in chemical structure are described below:

(1) The release of compounds cannot be controlled because of a large difference in boiling point (vapor pressure) due to a difference in functional group.

(2) The release of compounds cannot be controlled because even if they are compounds having the same functional group, they differ greatly in a boiling point (vapor pressure) owing to a difference in the number of carbon atoms.

(3) A formulation supported on a porous carrier having no barrier properties will inevitably release a compound having a higher vapor pressure faster even if an evaporation area is made equal. An additional difficulty in designing a releaser for simultaneous control of insect pests is that these insect pests have their own infestation period.

Among pest insects, there are many insect pests having an aldehyde compound as a sex pheromone substance, for example, *Chilo suppressalis, Helicoverpa assulta, Helicoverpa aarmigera*, diamondback moth, *Caloptilia theivora Walsingham, Dichocrocids punctiferalis Guenee*, navel orange worm, spiny bollworm and *Parapediasia teterrella*.

SUMMARY OF THE INVENTION

In general, aldehyde compounds tend to be deteriorated to a large extent by oxidation, polymerization or the like because of their structural characteristics. The present inventors have found that such deterioration is increased in the presence of a linear aliphatic acetate having at least two double bonds such as conjugated diene and 1,4-pentadiene-based compounds.

When release of a mixed sex pheromone solution filled in a conventional polymer container, containing together with an aldehyde compound, an alcohol compound and/or an acetate compound having a conjugate diene structure or 1,4-pentadiene structure, is controlled and sex pheromone substances having different chemical structures of one insect pest or sex pheromone substances of a plurality of inset pests are mixed, not only it is difficult to release the mixture while keeping the same composition ratio as the starting composition ratio at the time of filling but also effects on mating disruption are markedly low because of a great loss of the aldehyde compound due to deterioration.

For example, in the turfgrass in Japan, it is usually indispensable to simultaneously control two insect pests, *Parapediasia teterrella* having aldehyde compounds of Z-11-hexadecenal and Z-9-hexadecenal as sex pheromone substances, and *Spodoptera exempta* having an 1,4-pentadiene acetate compound of Z,E-9,12-tetradecadienyl acetate and Z-9-tetradecenyl acetate as sex pheromone substances. Sustained releasers exhibiting stable mating-disruption effects have not yet been developed.

On the other hand, as one measure for simultaneously disrupting the mating of a plurality of insect pests, designing each releaser (dispenser) for each insect pest and then placing it during each infestation period of the each insect pest are considered. However, it raises the cost of the releaser and requires a large labor for the placement of releasers. Consequently, it goes against the labor-saving effects in agriculture.

There is accordingly a demand for the development of a labor-saving sustained releaser capable of successfully releasing sex pheromone substances when sex pheromone substances having different chemical structures of one insect pest are mixed or sex pheromone substances of a plurality of insect pests are mixed.

An object of the present invention is to enable control of simultaneous release when sex pheromone substances having different chemical structures of one insect pest or sex pheromone substances of a plurality of pest insects are mixed and to prevent deterioration of an aldehyde compound as a sex pheromone substance particularly in the presence of an alcohol compound and/or acetate. Another object of the present invention is to provide a sustained releaser and a pest control method capable of releasing a mixture of sex pheromone substances of a plurality of insect pests at a fixed rate or greater during the infestation period or periods of the respective insect pests.

With a view to overcoming the above problems, the present inventors investigated a sustained releaser of sex pheromone substances capable of controlling the simultaneous release of sex pheromone substances of a plurality of insect pests; capable of preventing deterioration of an aldehyde compound particularly in the presence of an alcohol compound and/or a compound such as acetate; and capable of releasing the sex pheromone substances at a fixed rate or greater during the infestation period of the respective insect pests. As a result, it has been found that the above object can be attained by enclosing all of one or more sex pheromone substances having at least one aldehyde or all of one or more sex pheromone substances having at least one aldehyde and some of sex pheromone substances having at least one alcohol or the like in one of two polymer chambers, and enclosing a remainder of the sex pheromone substances in the other polymer chamber, preferably integrating these chambers into one while placing them in parallel to each other, leading to the completion of the present invention.

In the present invention, there is thus provided a sustained releaser of sex pheromone substances, comprising one or more first sex pheromone substances selected from linear aliphatic aldehyde having 10 to 18 carbon atoms, one or more second sex pheromone substances selected from aldehyde-free aliphatic derivatives having 7 to 20 carbon atoms, and first and second chambers each made of polymer material, wherein all of the first sex pheromone substances or all of the first sex pheromone substances and some of the second sex pheromone substances are enclosed in the first chamber and the remainder of the sex pheromone substances are enclosed in the second chamber.

In the present invention, there is also provided a chamber adapted for a sustained releaser of sex pheromone substances, the releaser comprising one or more first sex pheromone substances selected from linear aliphatic aldehydes having from 10 to 18 carbon atoms, one or more second sex pheromone substances selected from aldehyde-free aliphatic derivatives having 7 to 20 carbon atoms, and first and second chambers each made of polymer material, wherein all of the first sex pheromone substances or all of the first sex pheromone substances and some of the second sex pheromone substances are enclosed in the first chamber and the remainder of the sex pheromone substances are enclosed in the second chamber.

The sustained releaser and the pest control method according to the present invention make it possible to control the simultaneous release of sex pheromone substances against insect pests, to prevent deterioration of an aldehyde compound as the sex pheromone substance particularly in the presence of alcohol and/or acetate, and to release the sex pheromone substances at a fixed rate or greater in accordance with the infestation period of the respective insect pest.

BRIEF DESCRIPTION OF THE DRAWING(S)

FIG. 1 illustrates the preparation step of the sustained releaser of the present invention. FIG. 1(a) illustrates two tubes of polymer material; FIG. 1(b) illustrates a joint of these tubes, FIG. 1(c) illustrates a sealing step by a heat sealer, and FIG. 1(d) is a cross-sectional view of the sustained releaser.

DETAILED DESCRIPTION OF THE PREFERRED EMBODIMENT(S)

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless: the context clearly indicates otherwise.

Unless otherwise defined, all technical and scientific terms used herein have the same meaning as commonly understood by one of ordinary skill in the art to which this invention belongs.

In the present invention, examples of sex pheromones of insect pests for turfgrasses in Japan are shown in Table 1.

TABLE 1

| Insect pest | Sex pheromone substance |
| --- | --- |
| *Parapediasia teterrella* | Z-11-hexadecenal |
| | Z-9-hexadecenal |
| *Spodoptera exempta* | Z-9-tetradecenyl acetate |
| | Z,E-9,12-tetradecadienyl acetate |

When the above compounds are enclosed in a narrow tube, capsule, laminate or the like made of polymer membrane (film) and the release of the compounds can be controlled while using the membrane as a barrier, difference in their release control factors of (1) vapor pressures of the enclosed sex pheromone substances and (2) affinity (solubility parameter) between the functional groups of the sex pheromone substances and the polymer material disturbs uniform release. In addition, because the remaining amount of the aldehyde compounds shows a drastic decrease owing to the acetalation between aldehyde compounds and alcohol compounds in the chamber (container), a reduction in the release rate occurs. Moreover, on the surface of the chamber, the deterioration of the aldehyde compounds is enhanced by the deterioration product of the compound having an 1,4-pentadiene structure as a result of exposure to ultraviolet rays, leading to a reduction in the release amount of the aldehyde compounds. At the same time, a barrier layer is inevitably formed on the surface of the chamber, leading to a marked reduction in the release of the other compounds.

The present inventors have therefore carried out various investigations. As a result, it has been found that when a plurality of sex pheromone substances having different chemical structures of one insect pest are mixed or sex pheromone substances of a plurality of insect pest are mixed, by enclosing all of one or more sex pheromone substances selected from linear aliphatic aldehyde having 10 to 18 carbon atoms or all of one or more sex pheromone substances selected from aliphatic linear aliphatic aldehyde having 10 to 18 carbon atoms and some of one or more pheromone substances selected from aldehyde-free aliphatic derivatives having 7 to 20 carbon atoms in a first chamber of polymer material and enclosing the remainder of one or more pheromone substances selected from aldehyde-free aliphatic derivatives having 7 to 20 carbon atoms in a second chamber of polymer material, preferably these chambers being integrated into one while joined in parallel to each other, it is possible to prevent deterioration of the aldehyde compound as a sex pheromone substance and to release, as well as this aldehyde sex pheromone substance, the other sex pheromone substance for a prolonged period, leading to the completion of the present invention.

Examples of the sex pheromone substance to be used in the present invention may include linear aliphatic aldehyde having 10 to 18 carbon atoms and aldehyde-free aliphatic derivatives having 7 to 20 carbon atoms.

Examples of the aldehyde-free aliphatic derivatives having 7 to 20 carbon atoms may include sex pheromone substances selected from a group consisting of *Lepidoptera* linear aliphatic alcohol having 7 to 20 carbon atoms, linear aliphatic acetate which have 12 to 20 carbon atoms and are saturated or have at least one double bond, linear aliphatic ketones having 10 to 20 carbon atoms, and aliphatic hydrocarbons having 10 to 20 carbon atoms.

The present invention is especially useful for the simultaneous release of linear aliphatic aldehyde and linear aliphatic alcohol having 7 to 20 carbon atoms and/or a linear aliphatic acetate having 12 to 20 carbon atoms and two or more double bonds.

Examples of the linear aliphatic aldehyde having 10 to 18 carbon atoms to be used in the present invention may include Z-5-decenal, 10-undecenal, n-dodecanal, Z-5-dodecenal, Z-7-dodecenal, Z-9-dodecenal, E9-dodecenal, E5Z10-dodecadienal, Z5E7-dodecadienal, Z5Z7-dodecadienal, E7Z9-dodecadienal, E8E10-dodecadienal, E8Z10-dodecadienal, Z8E10-dodecadienal, E9,E11-dodecadienal, Z9,11-dodecadienal, n-tetradecanal, Z5-tetradecenal, Z7-tetradecenal, Z9-tetradecenal, E11-tetradecenal, Z11-tetradecenal, E8Z10-tetradecadienol, E8E10-tetradecadienal, Z9E11-tetradecadienal, Z9Z11-tetradecadienal, Z9E12-tetradecadienal, 10,12-tetradecadienol, E11,13-tetradecadienal, Z11,13-tetradecadienal, Z9E11,13-tetradecatrienol, Z10-pentadecenal, E9Z11-pentadecadienal, n-hexadecanal, Z7-hexadecenal, Z9-hexadecenal, E10-hexadecenal, Z10-hexadecenal, E11-hexadecenal, Z11-hexadecenal, Z12-hexadecenal, E6Z11-hexadecadienal, Z7E11-hexadecadienal, Z7Z11-hexadecadienal, E9Z11-hexadecadienal, Z9E11-hexadecadienal, Z9E12hexadecadienal, E10E12-hexadecadienal, E10Z12-hexadecadienal, Z10E12-hexadecadienal, Z10Z12-hexadecadienal, E11E13-hexadecadienal, E11Z13-hexadecadienal, Z11E13-hexadecadienal, Z11Z13-hexadecadienal, Z13-hexadecen-11-enal, E4E6Z11-hexadecatrienal, E10E12E14-hexadecatrienal, E10E12Z14-hexadecatrienal, n-octadecanal, E2-octadecenal, Z9-octadecenal, E11-octadecenal, Z11-octadecenal, E13-octadecenal, Z13-octadecenal, E14-octadecenal, E2Z13-octadecadienal, Z3Z13-octadecadienal, Z9Z12-octadecadienal, E11E14-octadecadienal, Z11Z13-octadecadienol, Z13Z15-octadecadienal, and Z9Z12Z15-octadecatrienaol.

The aldehyde-free aliphatic derivative having 7 to 20 carbon atoms according to the present invention may be a preferably sex pheromone substance selected from a group consisting of linear aliphatic alcohol having 7 to 20 carbon atoms and linear aliphatic acetate having 12 to 20 carbon atoms with two or more double bonds. It may be preferable it is not mixed with a sex pheromone substance selected from linear aliphatic aldehyde having 10 to 18 carbon atoms.

The linear aliphatic alcohol having 7 to 20 carbon atoms may preferably include saturated linear aliphatic alcohol and linear aliphatic alcohol having one or more double bonds. Specific examples may include n-heptanol, Z4-heptenol, Z6-nonenol, Z6,8-nonadienol, E6,8-nonadieol, n-decanol, Z5-decenol, E5-decenol, n-undecanol, undecenol, 11-chloro-E8E10-undecadienol, n-dodecanol, Z5-dodecenol, Z7-dodecenol, E7-dodecenol, Z8-dodecenol, E8-dodecenol, Z9-dodecenol, E9-dodecenol, E10-dodecenol, 11-dodecenol, Z5E7-dodecadienol, E5Z7-dodecadienol, E5E7-dodecadienol, Z7Z9-dodecadienol, Z7E9-dodecadienol, E7Z9-dodecadienol, Z8Z10-dodecadienol, Z8E10-dodecadienol, E8Z10-dodecadienol, E8E10-dodecadienol, 8,9-difluoro-E8E10-dodecadienol, 10,11-difloro-E8E10-dodecadienol, 8,9,10,11-tetrafluoro-E8E10-dodecadienol, Z9,11-dodecadienol, E9,E11-dodecadienol, n-tridecanol, n-tetradecanol, Z5-tetradecenol, E5-tetradecenol, Z7-tetradecenol, Z8-tetradecenol, Z9-tetradecenol, E9-tetradecenol, Z11-tetradecenol, E11-tetradecenol, Z9Z11-tetradecadienol, Z9E11-tetradecadienol, Z9Z12-tetradecadienol, Z9E12-tetradecadienol, Z10Z12-tetradecadienol, E10E12-tetradecadienol, n-pentadecanol, 6,10,14-trimethyl-2-pentadecanol, n-hexadecanol, Z9-hexadecenol, Z11-hexadecenol, E11-hexadecenol, Z7Z11-hexadecadienol, Z7E11-hexadecadienol, E10Z12-hexadecadienol, E10E12-hexadecadienol, Z11Z13-hexadecadienol, Z11E13-hexadecadienol, E11Z13-hexadecadienol, E11E13-hexadecadienol, Z13-hexadecen-11-en-ol, E4Z6Z10-hexadecatrienol, E4E6Z10-hexadecatrienol, n-octadecanol, Z13-octadecenol, E2Z13-octadecadienol, Z3Z13-octadecadienol, E3Z13-octadecadienol and n-eicosanol.

The aldehyde-free linear aliphatic acetate having 12 to 20 carbon atoms with two or more double bonds may preferably include an acetate compound having a conjugated diene structure and/or an 1,4-pentadiene structure. Specific examples may include Z3E5-decadienyl acetate, E3E5-decadienyl acetate, Z7,9-decadienyl acetate, Z3E5-dodecadienyl acetate, E3Z5-dodecadienyl acetate, Z5E7-dodecadienyl acetate, E5Z7-dodecadienyl acetate, Z9Z9-dodecadienyl acetate, Z7E9-dodecadienyl acetate, E7Z9-dodecadienyl acetate, E7E9-dodecadienyl acetate, Z8Z10-dodecadienyl acetate, Z8E10-dodecadienyl acetate, E8Z10-dodecadienyl acetate, E8E10-dodecadienyl acetate, 9,11-dodecadienyl acetate, E4Z7-tridecadienyl acetate, 11-methyl-Z9,12-tridecadienyl acetate, E3E5-tetradecadienyl acetate, E8E10-tetradecadienyl acetate, Z9Z11-tetradecadienyl acetate, Z9E11-tetradecadienyl acetate, E9Z11-tetradecadienyl acetate, E9E11-tetradecadienyl acetate, Z9Z12-tetradecadienyl acetate, Z9E12-tetradecadienyl acetate, E9E12-tetradecadienyl acetate, Z10Z12-tetradecadienyl acetate, Z10E12-tetradecadienyl acetate, E10Z12-tetradecadienyl acetate, E10E12-tetradecadienyl acetate, E11,13-tetradecadienyl acetate, Z8Z10-pentadecadienyl acetate, Z8E10-pentadecadienyl acetate, E8Z10-pentadecadienyl acetate, E8E10-pentadecadienyl acetate, Z8Z10-hexadecadienyl acetate, Z10E12-hexadecadienyl acetate, E10Z12-hexadecadienyl acetate, E10E12-hexadecadienyl acetate, Z11Z13-hexadecadienyl acetate, Z11E13-hexadecadienyl acetate, E11Z13-hexadecadienyl acetate, E11E13-hexadecadienyl acetate and Z11E14-hexadecadienyl acetate.

The aldehyde-free aliphatic derivative having 7 to 20 carbon atoms may be preferably a sex pheromone substance selected from a group consisting of linear aliphatic acetate which has 12 to 20 carbon atoms and is saturated or has a double bond; linear aliphatic ketone having 10 to 20 carbon atoms; and aliphatic hydrocarbon having 10 to 20 carbon atoms. It may be mixed with a sex pheromone substance selected from linear aliphatic aldehyde having 10 to 18 carbon atoms.

Examples of the aldehyde-free linear aliphatic acetate which has 12 to 20 carbon atoms and is saturated or has a double bond may include decyl acetate, Z3-decenyl acetate, E4-decenyl acetate, Z4-decenyl acetate, E5-decenyl acetate, Z5-decenyl acetate, E7-decenyl acetate, Z7-decenyl acetate, undecyl acetate, Z7-undecenyl acetate, Z8-undecenyl acetate, E9-undecenyl acetate, Z9-undecenyl acetate, dodecyl acetate, E3-dodecenyl acetate, Z3-dodecenyl acetate, E4-dodecenyl acetate, E5-dodecenyl acetate, Z5-dodecenyl acetate, E7-dodecenyl acetate, Z7-dodecenyl acetate, E8-dodecenyl acetate, Z8-dodecenyl acetate, E9-dodecenyl acetate, Z9-dodecenyl acetate, E10-dodecenyl acetate, Z10-dodecenyl acetate, 11-dodecenyl acetate, 10-methyldodecenyl acetate, tridecyl acetate, E3-tridecenyl acetate, E4-tridecenyl acetate, Z4-tridecenyl acetate, E6-tridecenyl acetate, E8-tridecenyl acetate, Z8-tridecenyl acetate, E9-tridecenyl acetate, Z9-tridecenyl acetate, Z10-tridecenyl acetate, E11-tridecenyl acetate, Z11-tridecenyl acetate, tetradecyl acetate, E3-tetradecenyl acetate, Z3-tetradecenyl acetate, E5-tetradecenyl acetate, Z5-tetradecenyl acetate, E6-tetradecenyl acetate, Z6-tetradecenyl acetate, E7-tetradecenyl acetate, Z7-tetradecenyl acetate, E8-tetradecenyl acetate, Z8-tetradecenyl acetate, E9-tetradecenyl acetate, Z9-tetradecenyl acetate, E10-tetradecenyl acetate, Z10-tetradecenyl acetate, E11-tetradecenyl acetate, Z11-tetradecenyl acetate, E12-tetradecenyl acetate, Z12-tetradecenyl acetate, 12-methyltetradecenyl acetate, pentadecyl acetate, Z8-pentadecenyl acetate, E9-pentadecenyl acetate, Z9-pentadecenyl acetate, Z10-pentadecenyl acetate, E12-pentadecenyl acetate, Z12-pentadecenyl acetate, hexadecyl acetate, Z3-hexadecenyl acetate, E5-hexadecenyl acetate, Z5-hexadecenyl acetate, E6-hexadecenyl acetate, Z7-hexadecenyl acetate, Z9-hexadecenyl acetate, Z10-hexadecenyl acetate, E11-hexadecenyl acetate, Z11-hexadecenyl acetate, Z12-hexadecenyl acetate, heptadecyl acetate, Z11-heptadecenyl acetate, octadecyl acetate, E2-octadecenyl acetate, Z11-octadecenyl acetate, and E13-octadecenyl acetate.

Examples of the aldehyde-free linear aliphatic ketone having 10 to 20 carbon atoms may include heptadecan-2-one, Z12-nonadecen-9-one, Z6Z9-nonadecadien-3-one, Z7-nonadecen-11-one, Z7-eicosen-11-one, Z6-heneicosen-11-one, Z6-heneicosen-9-one, Z6E8-heneicosadien-11-one, Z6E9-heneicosadien-11-one, Z6Z9-heneicosadien-11-one and Z7-tricosan-11-one.

Examples of the aldehyde-free aliphatic hydrocarbon having 10 to 20 carbon atoms may include 1E11-pentadecadiene, 1Z11-pentadecadiene, 5,9-dimethylpentadecane, 2-methylhexadecane, 3,13-dimethylhexadecane, 5,9-dimethylhexadecane, n-heptadecane, 2-methylheptadecane, 2,5-dimethylheptadecane, 3,13-dimethylheptadecane, 5-methylheptadecane, 5,11-dimethylheptadecane, 5,9-dimethylheptadecane, 7-methylheptadecane, 7,11-dimethylheptadecane, Z3Z6Z9-heptadecatriene, Z6Z9-heptadecadiene, Z7-octadecene, 10,14-dimethyl-1-octadecene, 14-methyl-1-octadecene, 2-methyl-Z7-octadecene, 5,9-dimethyloctadecane, 2-methyloctadecane, 14-methyloctadecane, Z3Z6Z9-octadecatriene, n-nonadecane, 2-methylnonadecane, 9-methylnonadecane, Z3Z6Z9E11-nonadecatetraene, Z3Z6Z9Z11-nonadecatetraene, 1E3Z6Z9-nonadecatetraene, 1Z3Z6Z9-nonadecatetraene, Z3Z6Z9-nonadecatriene, Z6Z9-nonadecadiene, Z9-nonadecene, n-eicosane, Z9-eicosene, Z3Z6-eicosadiene, Z6Z9-eicosadiene, Z3Z6Z9-eicosatriene, 1Z3Z6Z9-eicosatetraene, 1Z3Z6Z9-heneicosatetraene, n-heneicosane, Z3Z6-heneicosadiene, Z6Z9-heneicosadiene, Z6Z9,20-heneicosatriene, Z3Z6Z9-heneicosatriene, Z6-13-methylheneicosene, Z9-heneicosene, n-docosaene, Z3Z6Z9-docosatriene, Z6Z9-docosadiene, n-tricosane, Z3Z6Z9-tricosatriene, Z6Z9-tridosadiene, n-tetracosane, n-pentacosane, Z3Z6Z9-pentacosatriene, n-hexacosane, n-heptacosane, n-octacosane and n-nonacosane.

The sustained releaser of the present invention may contain a stabilizer such as an antioxidant or an ultraviolet absorber, or a colorant, keeping its content 10% by weight or less.

The sustained releaser of sex pheromones according to the present invention, for example, against *Parapediasia teterrella* and *Spodoptera exempta* which are insect pests found in the turfgrass in Japan as shown in Table 1, can be obtained by enclosing both Z-11-hexadecenal and Z-9-hexadecenal which are sex pheromone substances containing aldehyde of *Parapediasia teterrella* and Z-9-tetradecenyl acetate which is a linear aliphatic acetate having a double bond in a first chamber made of polymer material, which chamber is separated from a second chamber, and enclosing the remaining substance of Z9E12-tetradecadienyl acetate in a second chamber made of polymer material.

Although the amount of the sex pheromone substance(s) to be enclosed in each chamber may differ depending on the release period of the sustained releaser, volatility of the sex pheromone substance, affinity with the polymer material which the chamber is made of, it may be preferably from 50 to 400 mg, more preferably from 150 to 300 mg in each of the first and the second chambers.

The polymer material to be used in the invention may include polyolefin, acrylic polymer, polyester, polyamide, methacrylic polymer, olefin-vinyl alcohol ester copolymer or the like. When the membrane of the polymer material is used as a barrier, tube obtained by a conventional extrusion method, capsule, bag, or laminate can be selected. A plasticizer, lubricant, stabilizer or colorant may be added when the material is formed or molded into such a shape. According to the invention, the polymer materials of which the two chambers are made may be the same or different as long as they can be joined in any form, preferably integrated into one.

No particular limitation is imposed on the shape of the chamber made of polymer material which is usable in the invention insofar as it permits enclosure therein of a sex pheromone substance. For example, the chamber may include a container, a narrow tube, capsule and laminate made of membrane of polymer material and can permit sustained release of the sex pheromone substance enclosed therein as the membrane works as a barrier.

An appropriate size of the polymer membrane can be selected depending on the physical properties of the sex pheromone substance to be filled in it. Thickness and the inside and outside diameters of the first and second chambers of polymer material or materials may be the same or different. The thickness, in particular, can be greatly influenced by the evaporation rate of the sex pheromone substance so that the appropriate thickness can be selected, depending on a necessary release period, vapor pressure and solubility parameter of the sex pheromone substance. However, it may be necessary to select an appropriate thickness from a practical range because a marked difference in thickness between the first chamber and the second chamber of polymer material or materials, for example, can make it difficult to seal each chamber in which the substance has been filled.

According to the invention, the structure of each of the first and the second polymer chambers is not particularly limited. The chambers can be chemically joined via heat seal or adhesive. Alternatively, they may be joined physically by using a tape or wire. Tube 1 to be used as a first chamber and tube 2 to be used as a second chamber, each made of a polymer material, may be independent as shown in FIG. 1(*a*), or joined via a joint 3 in parallel to each other as shown in FIG. 1(*b*). The ends of two tubes may be chemically or physically connected using a heat sealer 4 as illustrated in FIG. 1(*c*) to obtain a sustained releaser containing sex pheromones A1 and A2 as illustrated in the cross-sectional view of FIG. 1(*d*). It should be noted that the invention is not limited to the chamber having such a structure.

The sustained releaser of the invention so far described has sex pheromone substances filled in first and second chambers. The present invention is not limited to it, but also embraces an embodiment in which a first chamber comprises a plurality of sub-chambers or a second chamber has a plurality of sub-chambers.

The present invention will hereinafter be described in detail by Examples and Comparative Examples. It should not be construed that the present invention is limited to or by them.

EXAMPLE 1

As a sustained releaser for controlling both *Parapediasia teterrella* and *Spodoptera exempta*, insect pests in the turfgrass in Japan, a 20 cm long tube releaser having the below-described tubes (A) and (B) in parallel to each other and being integrated into one as illustrated in FIG. 1 was prepared. Release of sex pheromones was confirmed in a thermostatic bath at 25° C. and 0.3 m/s. A change in a residual percentage of each sex pheromone substance in relation to the number of days elapsed is shown in Table 2.

Tube (A): A high-density polyethylene tube with an inside diameter of 1.43 mm and outside diameter of 2.73 mm (tube thickness: 0.65 mm) having the below-described components filled therein:
  Z-11-hexacenal: 210 mg
  Z-9-hexadecenal: 10 mg
  Z-9-tetradecenyl acetate: 30 mg Tube (B): A high-density polyethylene tube with an inside diameter of 1.37 mm and outside diameter of 2.67 mm (tube thickness: 0.65 mm) having the below-described components filled therein:
  Z-9-tetradecenyl acetate: 170 mg
  Z,E-9,12-tetradecadienyl acetate: 50 mg
  Z-11-hexadecenol: 10 mg

COMPARATIVE EXAMPLE 1

An aluminum wire was bonded to a 20 cm long high-density polyethylene tube with an inside diameter of 1.40 mm and outside diameter of 2.70 mm (thickness of 0.65 mm) to give it formability. A uniformly mixed solution of all the sex pheromone substances used in Example 1 was filled in the tube and a time-dependent change of the residual percentage of each sex pheromone component was measured under similar conditions to those employed in Example 1. The results are shown in Table 2.

TABLE 2

| | Residual percentage of Z-11-hexadecenal (%) | | | |
|---|---|---|---|---|
| | 0 day Elapsed | 88 days elapsed | 143 days elapsed | 203 days elapsed |
| Example 1 | 100 | 53.7 | 29.6 | 10.3 |
| Comp. Ex. 1 | 100 | 56.5 | 32.0 | 28.0 |

The invention claimed is:

1. A sustained release dispenser of sex pheromone substances comprising:
   first and second chambers, each made entirely of a sex pheromone-permeable polymer material, wherein the polymer material that the first and second chambers are made of is the same, and wherein said polymer material is selected from the group consisting of polyolefins, acrylic polymers, polyesters, polyamides, methacrylic polymers and olefin-vinyl alcohol ester copolymers;
   (i) one or more linear aliphatic aldehydes having 10 to 18 carbon atoms, and (ii) one or more aldehyde-free saturated or one double bond-containing linear aliphatic acetates having 12 to 20 carbon atoms contained in the first chamber; and
   one or more aldehyde-free conjugated diene or 1,4-pentadiene structure-containing linear aliphatic acetates having 12 to 20 carbon atoms contained in the second chamber.

* * * * *